United States Patent
Scott et al.

(10) Patent No.: US 10,219,945 B2
(45) Date of Patent: Mar. 5, 2019

(54) LASER FIDUCIALS FOR AXIS ALIGNMENT IN CATARACT SURGERY

(71) Applicant: OptiMedica Corporation, Santa Ana, CA (US)

(72) Inventors: David D. Scott, Oakland, CA (US); David Dewey, Sunnyvale, CA (US); Javier Gonzalez, Palo Alto, CA (US)

(73) Assignee: Optimedica Corporation, Santa Ana, CA (US)

( * ) Notice: Subject to any disclaimer, the term of this patent is extended or adjusted under 35 U.S.C. 154(b) by 1226 days.

(21) Appl. No.: 14/255,430

(22) Filed: Apr. 17, 2014

(65) Prior Publication Data

US 2014/0343541 A1    Nov. 20, 2014

Related U.S. Application Data

(60) Provisional application No. 61/813,172, filed on Apr. 17, 2013.

(51) Int. Cl.
| | |
|---|---|
| *A61F 9/008* | (2006.01) |
| *A61F 2/16* | (2006.01) |
| *A61B 90/20* | (2016.01) |
| *A61B 90/00* | (2016.01) |

(52) U.S. Cl.
CPC ............. *A61F 9/008* (2013.01); *A61B 90/20* (2016.02); *A61B 90/37* (2016.02); *A61B 90/39* (2016.02); *A61F 2/16* (2013.01); *A61F 9/00834* (2013.01); *A61B 2090/363* (2016.02); *A61B 2090/3937* (2016.02); *A61F 2009/00878* (2013.01); *A61F 2009/00887* (2013.01); *A61F 2009/00889* (2013.01)

(58) Field of Classification Search
CPC ............... A61F 2/1662; A61F 9/00754; A61F 2009/00848; A61F 2009/00851; A61F 2009/00882; A61F 2009/00887; A61F 2009/00889; A61F 9/008; A61B 90/39; A61B 2090/363; A61B 2090/3937
See application file for complete search history.

(56) References Cited

U.S. PATENT DOCUMENTS

| | | | |
|---|---|---|---|
| 5,459,570 | A | 10/1995 | Swanson et al. |
| 5,720,894 | A | 2/1998 | Neev et al. |
| 5,748,352 | A | 5/1998 | Hattori |
| | | (Continued) | |

FOREIGN PATENT DOCUMENTS

| | | |
|---|---|---|
| WO | WO-2006009021 A1 | 1/2006 |
| WO | 2009059251 A2 | 5/2009 |
| WO | WO-2011163507 A2 | 12/2011 |

OTHER PUBLICATIONS

International Search Report and Written Opinion for Application No. PCT/US2014/34508, dated Jul. 30, 2014, 11 pages.

*Primary Examiner* — Howie Matthews
(74) *Attorney, Agent, or Firm* — Johnson & Johnson Surgical Vision, Inc.

(57) ABSTRACT

A fiducial is generated on an internal anatomical structure of the eye of a patient with a surgical laser. A toric artificial intraocular lens (IOL) is positioned so that a marker of the toric IOL is in a predetermined positional relationship relative to the fiducial. This positioning aligns the toric IOL with the astigmatic or other axis of the eye. The toric IOL is then implanted in the eye of the patient with high accuracy.

23 Claims, 10 Drawing Sheets

(56) References Cited

U.S. PATENT DOCUMENTS

| | | | |
|---|---|---|---|
| 5,748,898 | A | 5/1998 | Ueda |
| 5,957,915 | A | 9/1999 | Trost |
| 5,984,916 | A | 11/1999 | Lai |
| 6,019,472 | A | 2/2000 | Koester et al. |
| 6,053,613 | A | 4/2000 | Wei et al. |
| 6,111,645 | A | 8/2000 | Tearney et al. |
| 6,454,761 | B1 | 9/2002 | Freedman |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,394,084 | B2 | 3/2013 | Blumenkranz et al. |
| 8,414,564 | B2 | 4/2013 | Goldshleger et al. |
| 8,475,433 | B2 | 7/2013 | Mrochen et al. |
| 2010/0137983 | A1* | 6/2010 | Culbertson ............... A61F 2/16 623/6.43 |
| 2010/0191226 | A1 | 7/2010 | Blumenkranz et al. |
| 2010/0274228 | A1 | 10/2010 | Mrochen et al. |
| 2011/0122365 | A1 | 5/2011 | Kraus et al. |
| 2011/0190739 | A1 | 8/2011 | Frey et al. |
| 2011/0319873 | A1 | 12/2011 | Raksi et al. |
| 2011/0319875 | A1 | 12/2011 | Loesel et al. |
| 2012/0078240 | A1* | 3/2012 | Spooner ............. A61F 9/00827 606/5 |
| 2012/0265181 | A1* | 10/2012 | Frey .................... A61B 3/1035 606/5 |
| 2012/0310223 | A1 | 12/2012 | Knox et al. |

\* cited by examiner

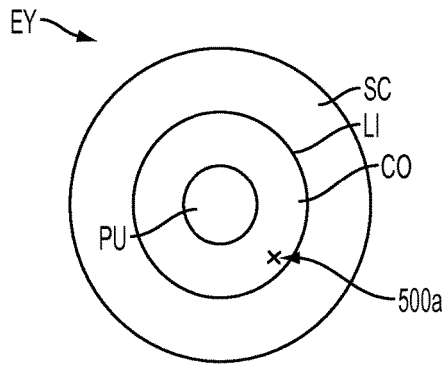
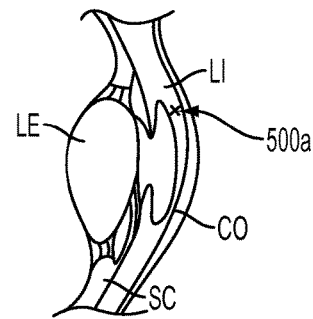
FIG. 5A1　　　　　　FIG. 5A2
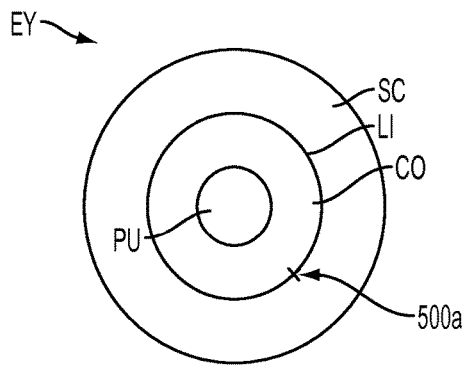
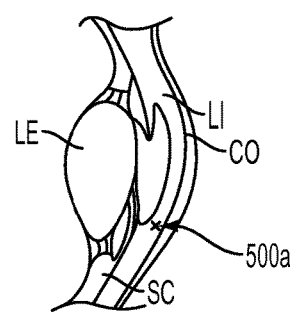
FIG. 5B1　　　　　　FIG. 5B2
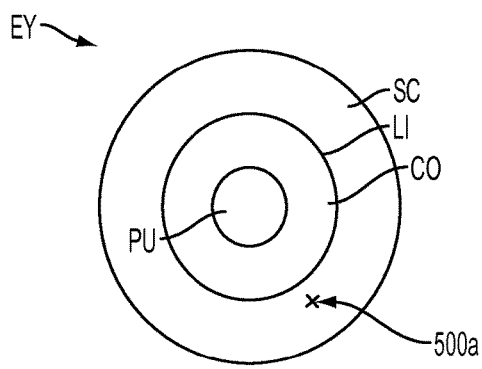
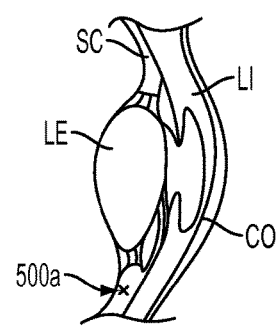
FIG. 5C1　　　　　　FIG. 5C2

LASER FIDUCIALS FOR AXIS ALIGNMENT IN CATARACT SURGERY

CROSS-REFERENCE

This application claims priority to U.S. provisional application No. 61/813,172 filed on Apr. 17, 2013, which is related to U.S. patent application Ser. No. 14/199,087, filed on Mar. 6, 2014, entitled "MICROFEMTOTOMY METHODS AND SYSTEMS," which claims priority to U.S. Provisional Application No. 61/788,201, the entire contents of which are incorporated herein by reference.

BACKGROUND

The present disclosure relates generally to the marking of anatomical features to facilitate the treatment of the nearby tissue structures, such as a tissue of an eye. Although specific reference is made to marking tissue for surgery such as eye surgery, embodiments as described herein can be used in many ways with many anatomical structures to facilitate the treatment of many tissue structures.

Cutting of materials can be done mechanically with chisels, knives, scalpels and other tools such as surgical tools. However, prior methods and apparatus of cutting can be less than desirable and provide less than ideal results in at least some instances. For example, at least some prior methods and apparatus for cutting materials such as tissue may provide a somewhat rougher surface than would be ideal. Pulsed lasers can be used to cut one or more of many materials and have been used for laser surgery to cut tissue.

Examples of surgically tissue cutting include cutting the cornea and crystalline lens of the eye. The lens of the eye can be cut to correct a defect of the lens, for example to remove a cataract, and the tissues of the eye can be cut to access the lens. For example the cornea can be to access the cataractous lens. The cornea can be cut in order to correct a refractive error of the eye, for example with laser assisted in situ keratomileusis (hereinafter "LASIK").

Many patients may have visual errors associated with the refractive properties of the eye such as nearsightedness, farsightedness and astigmatism. Astigmatism may occur when the corneal curvature is unequal in two or more directions. Nearsightedness can occur when light focuses before the retina, and farsightedness can occur with light refracted to a focus behind the retina. There are numerous prior surgical approaches for reshaping the cornea, including laser assisted in situ keratomileusis (hereinafter "LASIK"), all laser LASIK, femto LASIK, corneaplasty, astigmatic keratotomy, corneal relaxing incision (hereinafter "CRI"), and Limbal Relaxing Incision (hereinafter "LRI"). Astigmatic Keratotomy, Corneal Relaxing Incision (CRI), and Limbal Relaxing Incision (LRI), corneal incisions are made in a well-defined manner and depth to allow the cornea to change shape to become more spherical.

Cataract extraction is a frequently performed surgical procedure. A cataract is formed by opacification of the crystalline lens of the eye. The cataract scatters light passing through the lens and may perceptibly degrade vision. A cataract can vary in degree from slight to complete opacity. Early in the development of an age-related cataract the power of the lens may increase, causing nearsightedness (myopia). Gradual yellowing and opacification of the lens may reduce the perception of blue colors as those shorter wavelengths are more strongly absorbed and scattered within the cataractous crystalline lens. Cataract formation may often progresses slowly resulting in progressive vision loss.

A cataract treatment may involve replacing the opaque crystalline lens with an artificial intraocular lens (IOL), and an estimated 15 million cataract surgeries per year are performed worldwide. Cataract surgery can be performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole can be formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye.

At least some prior laser surgery systems can provide less than ideal results when used to place an intraocular lens in the eye to treat aberrations of the eye such as low order aberrations comprising astigmatism or higher order aberrations. While accommodating IOLs can correct refractive error of the eye and restore accommodation, the prior accommodating IOLs can provide less than ideal correction of the astigmatism of the eye.

Thus, improved methods and systems would be helpful for more precisely marking and tracking anatomical features in tissue, particularly the eye, to better position tissue cuts and place implants such as intraocular lenses (IOLs) in the eye.

SUMMARY

Embodiments as described herein provide improved methods and apparatus of marking and tracking the tissue structures such as the eye, in many embodiments to facilitate surgical procedures for the eye such as the implantation of an artificial intraocular lens (IOL) or other lens placed with the eye. In many embodiments, a fiducial is generated on an anatomical structure of the eye in order to position an axis of the IOL with an axis of the eye. In many embodiments, an implantable lens device comprises a marker, and the implantable lens device is positioned so that the marker of the implantable device is placed in a positional relationship relative to the fiducial. In many embodiments, the implantable device comprises an artificial intraocular lens such as a toric intraocular lens which can treat astigmatism of the eye. Positioning the implantable device so that the fiducial is in the positional relationship relative to the fiducial can comprise aligning the axis of the implantable device with an axis of the eye, such as an astigmatic axis of the eye.

In a first aspect, a method of implanting an implantable device in an eye of a patient is provided. A fiducial is generated on an anatomical structure of the eye. The implantable device is placed so that a marker of the implantable device is in a positional relationship relative to the fiducial.

In many embodiments, the eye is retained with a patient interface coupled to the eye with suction. The fiducial can be generated when the eye is retained with the patient interface. In some cases, the patient interface may distort one or more tissue structures in the eye which can lead to inaccurate fiducial generation. Thus, the fiducial can alternatively be generated prior to retaining the eye with the patient interface.

In many embodiments, the implantable device comprises an intraocular lens. The marker of the intraocular lens and the fiducial generated on the eye can be visible to a user with a camera image or an operating microscope image provided to the user when the intraocular lens has been placed.

A user can input a treatment axis of an astigmatism of the eye. A first fiducial and a second fiducial can be generated on an internal anatomical structure of the eye to define the treatment axis extending across a pupil of the eye. The marker can comprises a first marker and a second marker placed on opposite sides of the implantable device to define a lens axis of an intraocular lens. The marker and the fiducial can be visible to a user to determine an alignment of the treatment axis with the lens axis. In some embodiments, the first fiducial and the second fiducial are located on the cornea away from an entrance pupil of the eye, and the first marker, the second marker, the first fiducial and the second fiducial are displayed in an image visible to a user.

A measurement structure of the eye can be measured with a laser system when the patient has been placed on a patient support of the laser system. The fiducial can be generated on the anatomical structure of the eye in response to the orientation of the measurement structure. The measurement structure of the eye can comprise one or more of a cornea of the eye, an iris of the eye or a crystalline lens of the eye and wherein the orientation comprises one or more of an angle of an astigmatic axis of the cornea, a rotational angle of the iris about a pupil of the eye or an astigmatic axis of the lens of the eye.

The implantable device can comprise an artificial intraocular lens such as a toric intraocular lens. The positional relationship can comprise a pre-determined positional relationship.

The implantable device can be positioned so that the fiducial in the positional relationship relative to the fiducial to align a vision correcting axis of the implantable device with an aberration axis of the eye. The aberration axis of the eye may comprise an astigmatic axis or an axis of a higher order aberration. And, the implantable device can corrects a higher order aberration of the eye comprising one or more of coma, trefoil or spherical aberration.

The marker of the implantable device and the fiducial placed on the internal anatomical structure of the eye can have many shapes, including one or more of a dot, a line, a rectangle, an arrow, a cross, a trapezoid, a rectangle, a square, a chevron, a pentagon, a hexagon, a circle, an ellipse, or an arc. The fiducial may have a shape corresponding to a shape of the marking of the implantable device. The shape of the fiducial may be similar to the shape of the marking. The shape of the fiducial may be complementary to the shape of the marking.

Typically, the fiducial is generated on the anatomical structure of the eye by marking the anatomical structure with a laser. The internal anatomical structure may comprise an internal structure of one or more of the limbus, the cornea, the sclera, in the lens capsule, the iris, the stroma, or in the crystalline lens nucleus. And, the internal structure can be visible to a user when implantable lens is placed. In many embodiments, the fiducial is generated at least on the periphery of the cornea or on the limbus.

At least two fiducials may be generated on the anatomical structure of the eye, for example, a first fiducial and a second fiducial can be generated. A shape of the first fiducial can be different from a shape of the second fiducial. A shape of the first fiducial can be the same as a shape of the second fiducial. The at least two fiducials can form a line corresponding to an axis of the eye and the implantable device can comprise at least two marks to determine a centration of the lens with respect to a pupil of the eye when the at least two marks are positioned near the at least two fiducials. The axis may comprise an astigmatic axis of the eye. The line formed from the at least two fiducials can be aligned with, parallel to, transverse to, or perpendicular to the axis of the eye.

In another aspect, an apparatus is provided. The apparatus comprises a laser to generate a laser beam, a scanner to scan the laser beam, and a processor operatively coupled to the laser and the scanner. The processor comprises a tangible medium configured with instructions to perform any variation of the above methods.

In yet another aspect, an apparatus for implanting an implantable device in an eye of the patient is provided. The apparatus comprises a laser to generate a laser beam, a scanner to scan the laser beam, and a patient interface. The scanner scans the laser beam onto the eye of a patient to generate a fiducial on an anatomical structure of the eye. The patient interface is coupled to the eye with suction. The apparatus can further comprise an operating microscope to provide an image of the generated fiducial to a user. The apparatus can further comprise a user input for inputting a treatment axis of an astigmatism of the eye. The scanner can be configured to generate a first fiducial and a second fiducial on an internal anatomical structure of the eye to define the treatment axis extending across a pupil of the eye.

BRIEF DESCRIPTION OF THE DRAWINGS

FIG. 5A1 shows a front view of the eye having a fiducial created thereon, in accordance with many embodiments;

FIG. 5A2 shows a side view of the front of the eye of FIG. 5A1;

FIG. 5B1 shows a front view of the eye having a fiducial created thereon, in accordance with many embodiments;

FIG. 5B2 shows a side view of the front of the eye of FIG. 5B1;

FIG. 5C1 shows a front view of the eye having a fiducial created thereon, in accordance with many embodiments;

FIG. 5C2 shows a side view of the front of the eye of FIG. 5C1;

DETAILED DESCRIPTION

Figure 1:
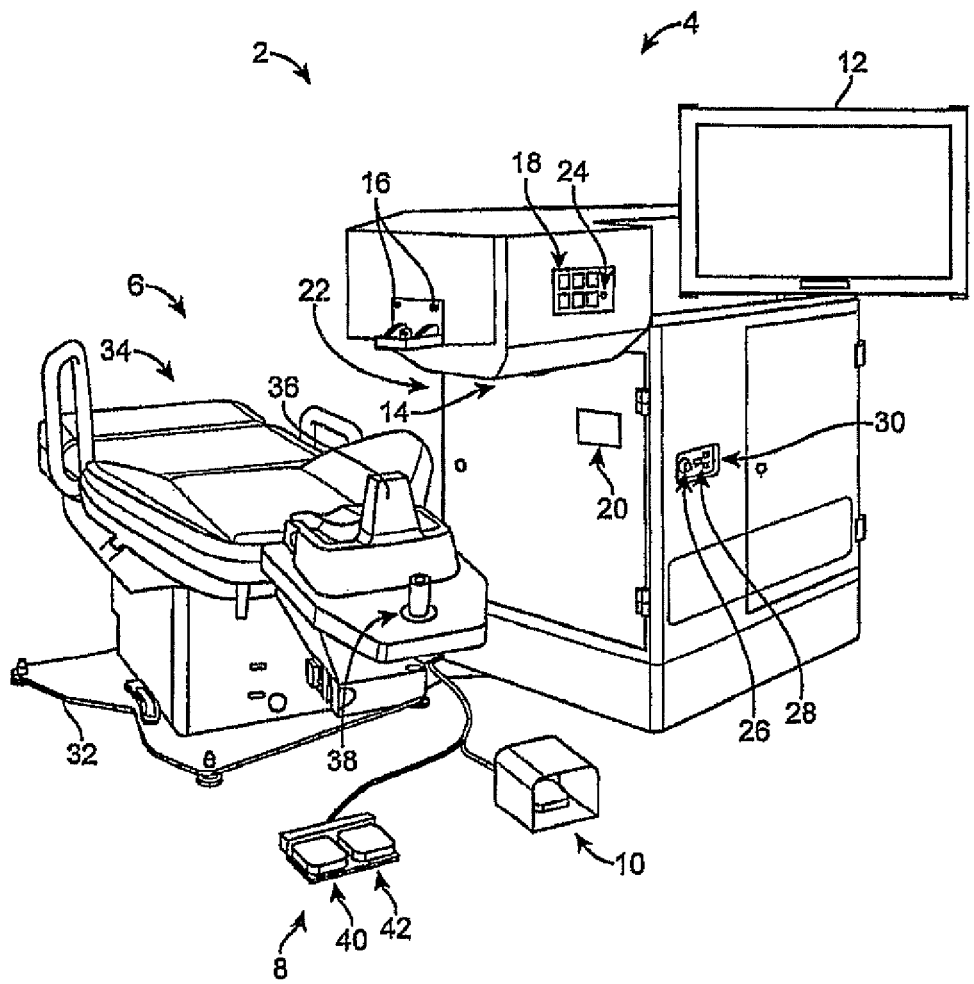
FIG. 1 shows a perspective view showing a laser eye surgery system, in accordance with many embodiments.

Methods and systems related to laser eye surgery are disclosed. In many embodiments, a laser is used to form precise incisions in the limbus, the cornea, in the lens capsule, the iris, the stroma, and/or in the crystalline lens nucleus. Although specific reference is made to tissue marking and alignment for laser eye surgery, embodiments as described herein can be used in one or more of many ways with many surgical procedures and devices, such as orthopedic surgery, robotic surgery and microkeratomes.

The embodiments as describe herein are particularly well suit for treating tissue, such as with the surgical treatment of tissue. In many embodiments, the tissue comprises an optically transmissive tissue, such as tissue of an eye. The embodiments as described herein can be combined in many ways with one or more of many known surgical procedures such as cataract surgery, laser assisted in situ keratomileusis (hereinafter "LASIK"), laser assisted subepithelial keratectomy (hereinafter "LASEK"), Methods and systems related to laser treatment of materials and which can be used with eye surgery such as laser eye surgery are disclosed. A laser may be used to form precise incisions in the cornea, in the lens capsule, and/or in the crystalline lens nucleus, for example. The embodiments as described herein can be particularly well suited for decreasing the amount of energy to the eye and increasing the accuracy of the cutting of the material such as tissue, for example.

The present disclosure provides methods and apparatus for providing adjustment to compensate for variations in disposable elements and other attachments, tolerances in hardware and alignment, and patient anatomy. The methods and apparatus may comprise a software look up table (hereinafter "LUT") embodied in a tangible medium. The LUT may comprise a map of locations of the cutting volume in order to the control of actuators that direct the ranging (target detection) and the cutting modalities. A baseline LUT can be generated for a generalized system using optical based rules and physics, detailed modeling of components, and anchoring (one time) to a finite data set as described herein. The expected variations can be reduced into a set of finite and manageable variables that are applied to modify the tables subsequent to the original generation of the tables. For a constructed system having constructed components with manufacturing tolerances, fine tuning and modification of the LUTs can be achieved thru simple modifications of the tables based on individual system and automated measurements. These individualized measurements of a constructed system can be applied to variations due to one or more of: tool-to-tool variation, tool to itself variation (for example align variations), output attachment variations (for example disposable contact lenses), or patient to patient (for example individual patient anatomy), and combinations thereof, for example.

In many embodiments, one or more of the following steps can be performed with the processor and methods as described herein. For example, baseline LUT generation can be performed comprising mapping and position detection in order to provide actuator commands to evaluate system output performance. A baseline transfer function can be generated for a patient coordinate reference system such as XYZ to detect actuators of the system, for example. Baseline LUT generation can be performed to map cutting to actuators. A transfer function can be generated for XYZ to cutting actuators, for example. Baseline LUTs (transfer functions) can be generated via model (ray trace), data, or a combination, for example. The baseline LUTs can be modified given variations in the system, disposable, eye, application, for example. The baseline LUT modification may comprise an adjustment to the baseline LUT, for example. The baseline LUT modification may comprise a software (hereinafter "SW") adjustment to compensate for hardware (hereinafter "HW") variations, for example. The LUT modification as described herein can extend surgical volume, so as to treat the cornea, the limbus and the posterior capsule, either in lateral extent, axial extent, and resolution, for example. The LUT methods and apparatus can enable switching in tools for calibration and other optical components to accessorize—output attachments, for example. The LUT can be set up so that the system is capable of measuring location of attachments at two surfaces and then can accurately place cuts in targeted material volume based on modifying the baseline LUT using this the locations of the two surfaces, for example. The LUTS can provide more cuts ranging from lens, capsule, corneal incisions for cataract, cornea flaps, for example. The different subsystems as described herein can have separate LUTS, which can be combined with calibration process as described herein, for example.

Alternatively, or in combination, the same sub-system can be used for both ranging and cutting, for example. The UF system can be used at a low power level to find surfaces and then used at high power for cutting, for example. The LUTs can be used such that the location mode differs from the cutting mode. For example, the cut locations can differ based on changes with power level. The cut location may not occur at focus, for example when the energy per pulse substantially exceeds the threshold amount of energy, for example.

In many embodiments, the LUTs of the methods and apparatus as described herein follow these principles. The baseline LUT can generated by ray tracing and data anchoring using specific tooling, for example. In many embodiments, each optically transmissive structure of the patient interface, for example a lens, is read by the system to determine its thickness and location. These numbers can be used to modify the LUTS to attain <100 um accuracy, for example.

In many embodiments, the LUTs of the methods and apparatus as described herein are also modified to account for alignment tilts, contact lens mounting, contact lens variations so as to achieve <100 um accuracy on cuts, for example. In many embodiments, a bubbles in plastic flatness test with the calibration apparatus as described herein generates offset and tilt adjustments of baseline UF LUT.

In many embodiments, the baseline component specifications may be less than ideal for delivering an appropriate system performance, and the final performance can be refined using SW corrections and factors based on the components of the individual system which can be determined from optically-grounded data-anchored baseline LUTs further modified for enhanced performance, for example.

A feedback loop can be used to build the enhanced or modified LUTs for the individual laser system, for example. The feedback methods and apparatus as described herein can allow SW adjustments based on LUTs and other SW factors that may not be corrected with hardware alignment, for example.

The LUTs and the methods an apparatus configured to modify the look up tables so as to enhance system performance can provide an improvement within the 3D surgical volume as described herein. The methods and apparatus as described herein can provide improved surgery for more patients with a level of high performance. The methods and apparatus as described herein can provide high performance using off-the-shelf components, such as high volume low cost components, such that the surgical procedures as described herein can be available to many patients.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
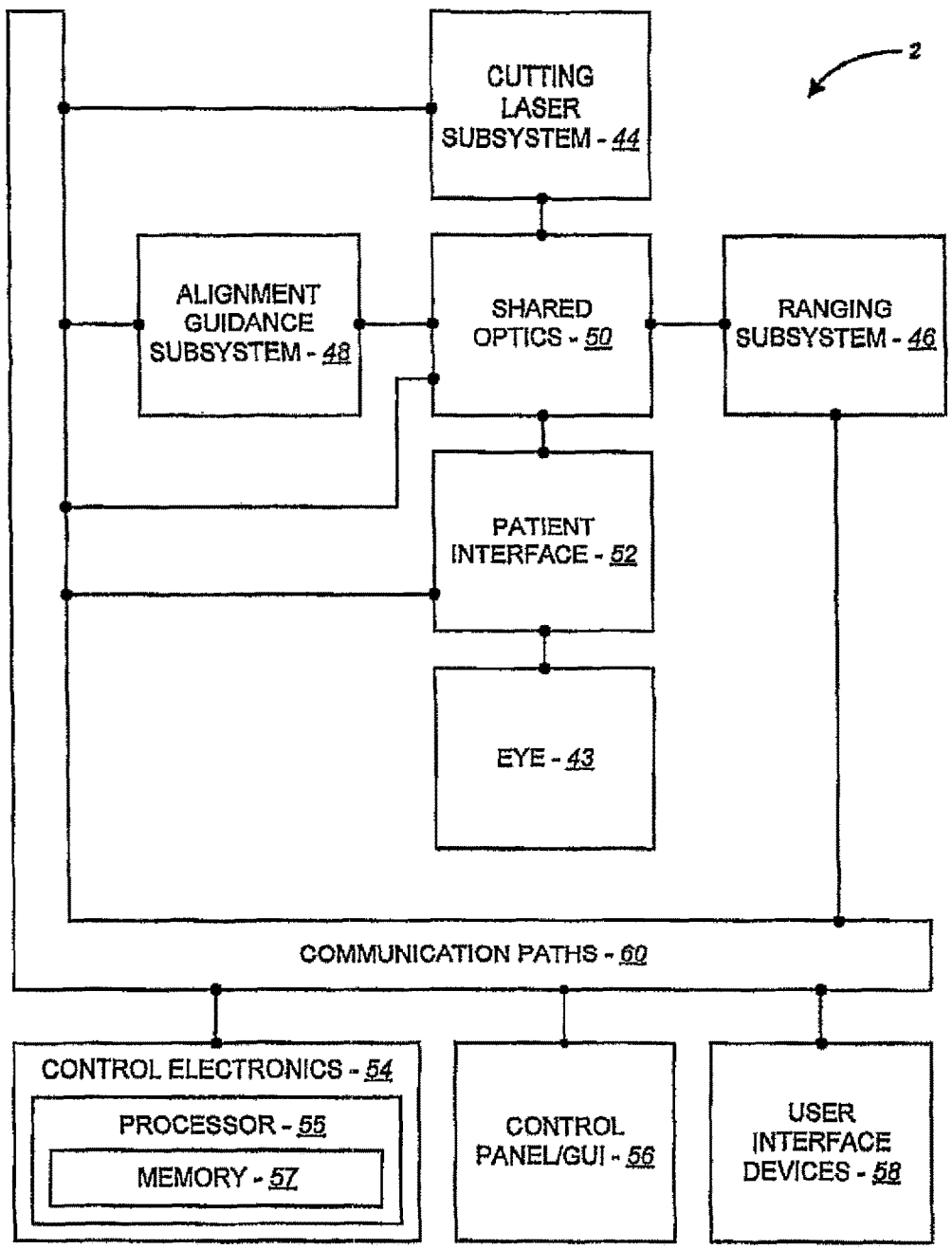
FIG. 2 shows a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea 43C, a lens 43L and an iris 431. The iris 431 defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3A:
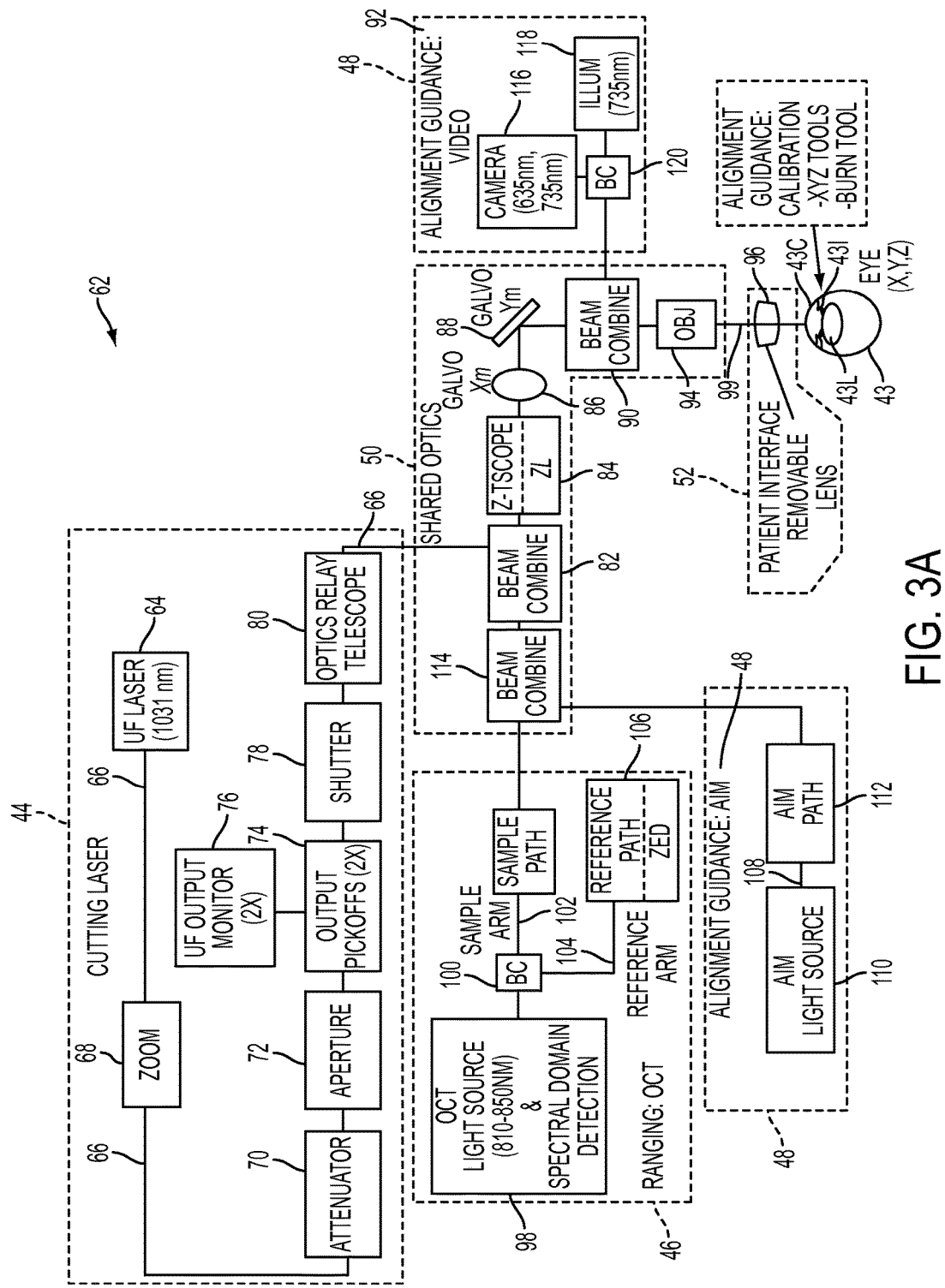
FIG. 3A shows a simplified block diagram illustrating the configuration of an optical assembly of a laser eye surgery system, in accordance with many embodiments.

FIG. 3A is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+7-5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials places on the docking structures and optical structures of the disposable lens such as the location of the anterior and posterior surfaces.

In the embodiment of FIG. 3A, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The ranging subsystem 46 in FIG. 3A includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the UF laser pulse beam 66 subsequent to the beam combiner 82, the OCT sample portion beam 102 follows a shared path with the UF laser pulse beam 66 through the shared optics 50 and the patient interface 52. In this way, the OCT sample portion beam 102 is generally indicative of the location of the UF laser pulse beam 66. Similar to the UF laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for a axially stationary surface in the eye of patient interface volume because the optical path length does not change as a function of different settings of the Z-telescope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 3A, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample portion beam 102 and the UF laser pulse beam 66 can be helpful with alignment provided the aim beam accurately represents the infrared beam parameters. The alignment guidance subsystem 48 is included in the assembly 62 shown in FIG. 3A. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 3B:
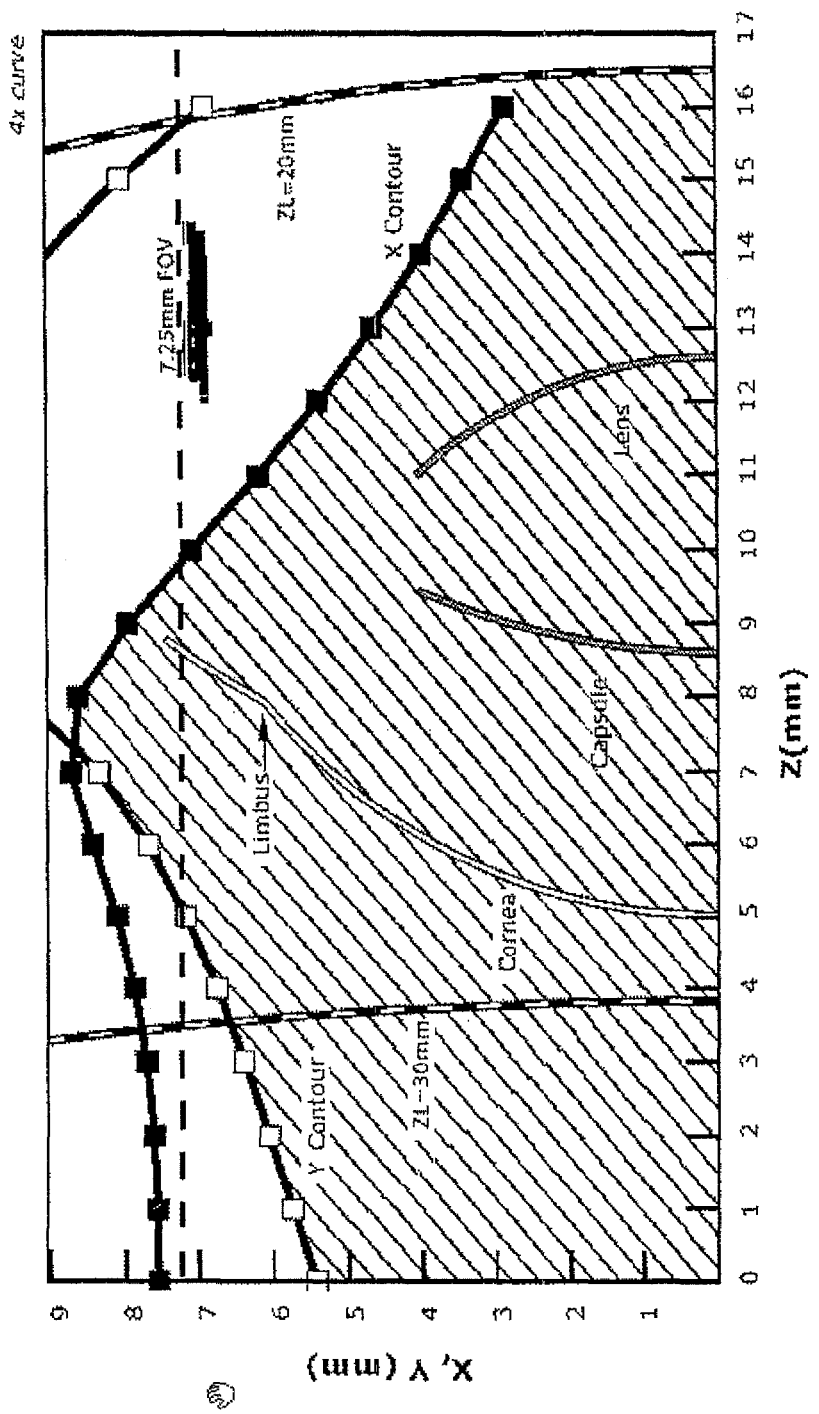
FIG. 3B shows a mapped treatment region of the eye comprising the cornea, the posterior capsule, and the limbus, in accordance with many embodiments.

FIG. 3B shows a mapped treatment region of the eye comprising the cornea, the posterior capsule, and the limbus. The treatment region can be mapped with computer modeling, for example ray tracing and phased based optical modeling. The treatment volume is shown extending along the Z-axis from the posterior surface of the optically transmissive structure of the patient interface a distance of over 15 mm, such that the treatment volume includes the cornea, and the lens in which the treatment volume of the lens includes the anterior capsule, the posterior capsule, the nucleus and the cortex. The treatment volume extends laterally from the cornea to the limbus. The lateral dimensions of the volume are defined by a Y contour anterior to the limbus and by an X contour posterior to the limbus. The treatment volume shown can be determined by a person of ordinary skill in the art based on the teachings described herein. The lateral positions of optical breakdown for ZL fixed to 30 mm and ZL fixed to 20 mm are shown. These surfaces that extend transverse to the axis 99 along the Z-dimension correspond to locations of optical scanning of the X and Y galvos to provide optical breakdown at lateral locations away from the axis 99. The curved non-planner shape of the scan path of optical breakdown for ZL-30 mm and ZL-20 mm can be corrected with the mapping and look up tables as described herein. The curved shape of the focus can be referred to as a warping of the optical breakdown depth and the look up tables can be warped oppositely or otherwise adjusted so as to compensate for the warping of the treatment depth, for example.

The treatment region is shown for setting the laser beam energy about four times the threshold amount for optical breakdown near the center of the system. The increased energy allows the beam system to treat the patient with less than ideal beam focus.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and look up tables as described herein can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

Figure 4:
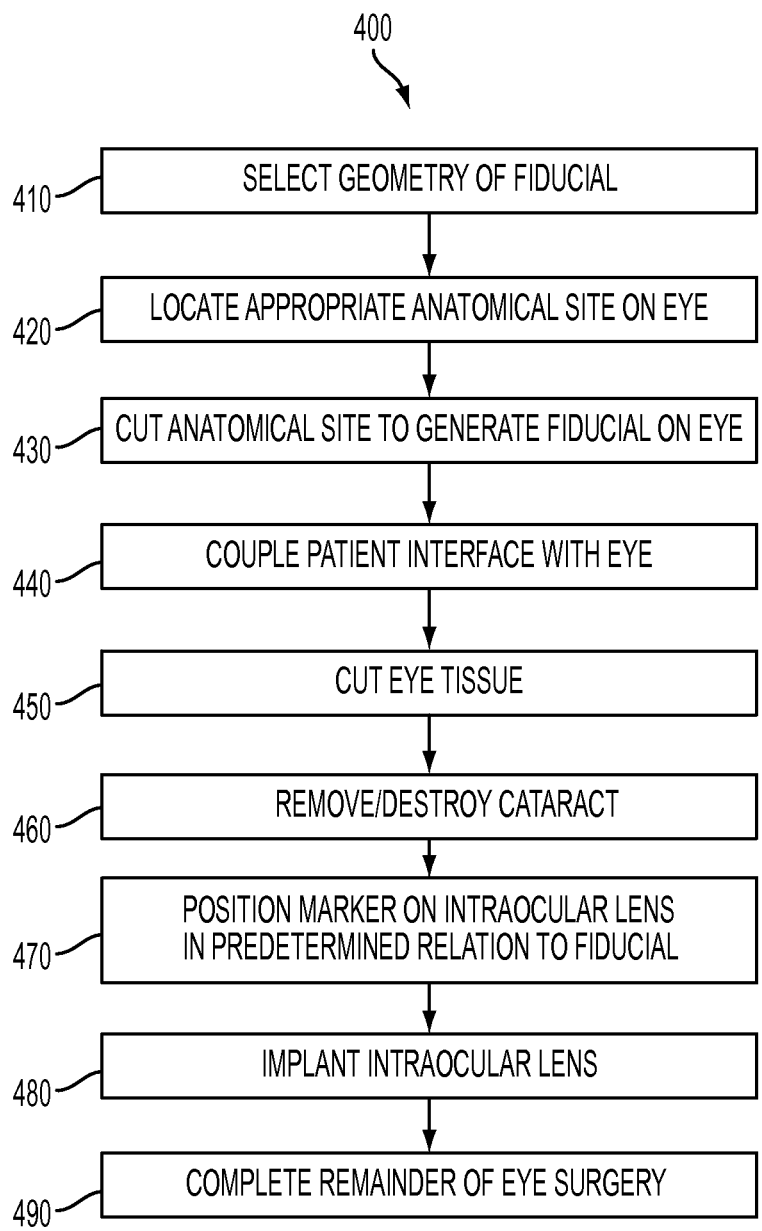
FIG. 4 shows a method of treating a patient, in accordance with many embodiments.

FIG. 4 shows a method 400 of treating a patient, for example with the laser eye surgery system 2 described herein, in accordance with many embodiments.

Examples of tissue treatment methods and apparatus suitable for combination in accordance with embodiments as described herein are described in U.S. patent application Ser. No. 12/510,148, filed Jul. 27, 2009, and Ser. No. 11/328,970, filed on Jan. 9, 2006, both entitled "METHOD OF PATTERNED PLASMA-MEDIATED LASER TREPHINATION OF THE LENS CAPSULE AND THREE DIMENSIONAL PHACO-SEGMENTATION," in the name of Blumenkranz et al., the full disclosures of which are incorporated by reference.

At a step 410, the geometry of one or more fiducials is selected. The fiducials may have a shape in the form of one or more dots, lines, rectangles, arrows, crosses, trapezoids, rectangles, squares, chevrons, pentagons, hexagons, circles, ellipses, arcs, and combinations thereof.

At a step 420, an appropriate anatomical site is located on the eye. This anatomical site may be located using the ranging subsystem 46 of the laser eye surgery system 2 described herein. Appropriate anatomical sites include, but are not limited to, the limbus, the cornea, the sclera, the lens capsule, the iris, the stroma, or the crystalline lens nucleus. In many embodiments, the appropriate anatomical site on the eye is the periphery of the cornea. Typically, the anatomical site will be in a predetermined position relative to an axis of the eye such as the astigmatic axis.

At a step 430, the anatomical site is marked and may be cut, for example, with the laser subsystem 44 of the laser eye surgery system 2, to generate the fiducial on the eye at the anatomical site located by step 420. One or more fiducials may be generated, for example, two fiducials to define a line in a known relation to an astigmatic axis of the eye or two or more fiducials to define more than one anatomical location of the eye.

At a step 440, a patient interface, for example, the patient interface 58 of the laser eye surgery system 2 described herein, is coupled with the eye often by suction. Any number of laser eye surgery procedures can now be performed. The fiducial generated on the eye can be used in such procedures to facilitate the precise positioning of treatment regimens, implantations, etc.

In many embodiments, cataract surgery is performed. For example, at a step 450, eye tissue is cut. At a step 460, a cataract is removed or destroyed, for example, using the procedures described in U.S. patent application Ser. Nos. 12/510,148 and 11/328,970, both entitled "METHOD OF PATTERNED PLASMA-MEDIATED LASER TREPHINATION OF THE LENS CAPSULE AND THREE DIMENSIONAL PHACO-SEGMENTATION," in the name of Blumenkranz et al. At a step 470, a marker on an artificial intraocular lens is positioned in a predetermined relation to the fiducial on the eye. The marker will typically have a geometry corresponding to that of the fiducial. The marker may have the same or complementary geometry as the fiducial. The predetermined relation may be one of linear alignment, for example, with a line formed by the fiducial and the center of the pupil or a line formed by two or more fiducials, or one where the marker is offset from such lines at a predetermined angle such as 30, 45, 60, or 90 degrees. At a step 480, the positioned intraocular lens is implanted. At a step 490, the remainder of the eye surgery is completed.

The placement of the IOL can proceed in accordance with known IOLs and methods modified in accordance with the teachings provided herein, and the IOL may comprise an accommodating or non-accommodating IOL, for example.

Although the above steps show method 400 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 400 may be performed with the circuitry as described herein, for example, one or more of the processor or logic circuitry such as the programmable array logic for field programmable gate array. The circuitry may be programmed to provide one or more of the steps of the method 400, and the program may comprise program instructions stored on a computer readable memory or programmed steps of the logic circuitry such as the programmable array logic or the field programmable gate array, for example.

As discussed above, one or more fiducials can be generated in various locations on the eye including various internal anatomical structures. For example, FIG. 5A1 shows a front view of the eye EY having a fiducial 500*a* generated thereon. As shown in FIGS. 5A1 and 5A2, a fiducial 500*a* having an X-shape is generated on the periphery of the cornea CO.

FIGS. 5B1 and 5B2 show a front view and a side view, respectively, of an eye EY having an X-shaped fiducial 500*a* generated on the limbus LI.

FIG. 5C1 sand 5B2 show a front view and a side view, respectively, of an eye EY having an X-shaped fiducial 500*a* generated on the sclera SC.

FIGS. 5A1 to 5C2 also show other anatomical features of the eye EY at or near the generated fiducial 500*a*, including the pupil FU and lens LE.

Figure 6:
FIG. 6 shows various configuration of fiducials, in accordance with many embodiments.

FIG. 6 shows various examples of shapes of fiducials in accordance with many embodiments. These fiducials can be cut onto the eye EY using a laser subsystem 44 of the laser eye surgery system 2 described herein. A fiducial 500*a* can be X-shaped. A fiducial 500*b* can be in the shape of a cross. A fiducial 500*c* can be in the form of a circular dot. A fiducial 500*d* can be in the shape of a circle. A fiducial 500*e* can be in the shape of a line segment. A fiducial 500*f* can be in the shape of a filled triangle. A fiducial 500*g* can be in the shape of an empty triangle. A fiducial 500*h* can be in the shape of a filled square. A fiducial 500*i* can be in the shape of an empty square. A fiducial 500*j* can be in the shape of a filled chevron. A fiducial 500*k* can be in the shape of an empty chevron. A fiducial 500*l* can be in the shape of a filled trapezoid. A fiducial 500*m* can be in the shape of an empty trapezoid. A fiducial 500*n* can be in the shape of a filled rectangle. A filled fiducial 500*o* can be in the shape of an empty rectangle. A fiducial 500*p* can be in the shape of a filled diamond. A fiducial 500*q* can be in the shape of an empty diamond. A fiducial 500*r* can be in the shape of a filled pentagon. A fiducial 500*s* can be in the shape of an empty pentagon. A fiducial 500*t* can be in the shape of a filled 5-pointed star. A fiducial 500*u* can be in the shape of an empty 5 pointed star. A fiducial 500*v* can be in the shape of a filled oval. A fiducial 500*w* can be in the shape of an empty oval. A fiducial 500*x* can be in the shape of a filled 6-pointed star. A fiducial 500*y* can be in the shape of an empty 6-pointed star. A fiducial 500*z* can be T-shaped.

FIGS. 7A to 7D show front views of one or more fiducials created on the eye EY positioned in pre-determined positional relationships with an artificial intraocular lens TOL.

A person of ordinary skill in the art will recognize that the IOL can be placed in the eye in accordance with known method and apparatus, and that the aberration correcting axis of the IOL and lens of the IOL will extend across pupil PU when placed, and that FIGS. 7A-7D show the IOL configured for placement positioning and alignment with the fiducials. The aberration corrected may comprise a lower order aberration such as astigmatism, or higher order aberration such as trefoil can coma. Further, the marker of the IOL may be used to define an axis of the lens to be aligned with the eye, for example an X, Y, or Z reference of the eye to be aligned with an X, Y or Z axis of a wavefront correcting IOL.

Figure 7A:
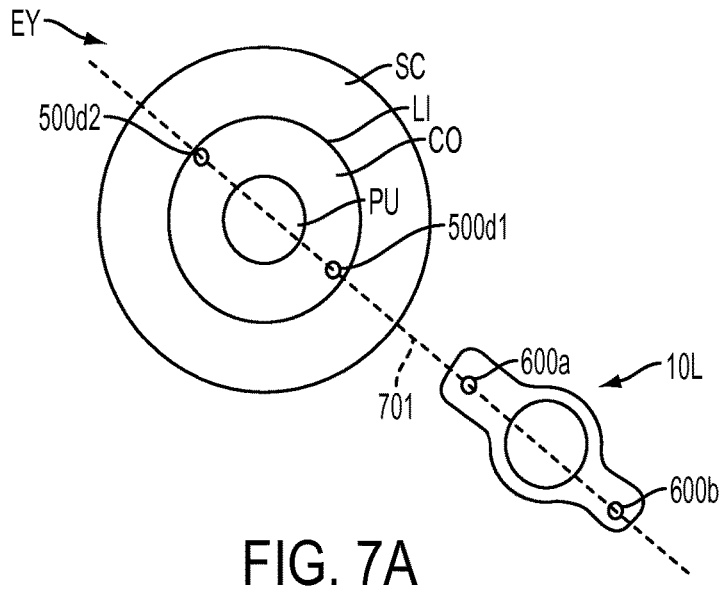
FIGS. 7A to 7D show front views of one or more fiducials created on the eye for placement in predetermined positional relationships with an artificial intraocular lens (TOL)

As shown in FIG. 7A, two circular fiducials 500*d*1, 500*d*2 can be generated on the periphery of the cornea CO of an eye EY. These two fiducials 500*d*1, 500*d*2 define a line 701 which may be aligned with or parallel to the astigmatic axis of the eye EY. The artificial intraocular lens IOL can be positioned so that markers 600*a*, 600*b* on the lens IOL can be aligned with the fiducials 500*d*1, 500*d*2 by being on the same line 701. The shape of the markers 600*a*, 600*b* can correspond to the shape of the fiducials 500*d*1, 500*d*2. For example in FIG. 7A, the markers 600*a*, 600*b* can be in the form of circular dots which may fit within the circles of the fiducials 500*d*1, 500*d*2 when the artificial intraocular lens IOL is properly positioned and aligned within the eye EY. Other complementary shapes may also be used to facilitate the positioning and alignment of the artificial intraocular lens IOL within the eye EY.

Figure 7B:
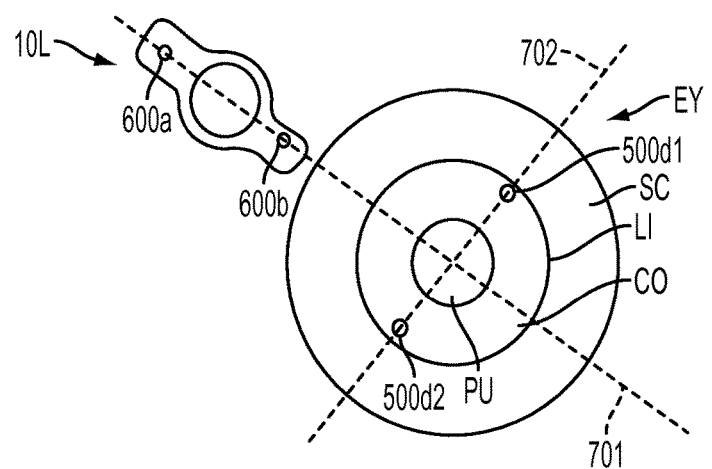

In some embodiments, the two fiducials 500*d*1, 500*d*2 can define a line 702 which may be perpendicular or otherwise transverse to the astigmatic axis of the eye EY. As shown in FIG. 7B, the artificial intraocular lens IOL can be positioned so that the markers 600*a*, 600*b* on the lens IOL form a line perpendicular to the line 702 formed by the fiducials 500*d*1, 500*d*2. Thus, the lens IOL can be properly positioned in alignment with the astigmatic axis of the eye EY. In other embodiments, the artificial intraocular lens IOL can be positioned so that the markers 600*a*, 600*b* on the lens IOL form a line transverse to the line 702 formed by the fiducials 500*d*1, 500*d*2, for example, at predetermined angles of 30 degrees, 45 degrees, or 60 degrees.

Figure 7C:
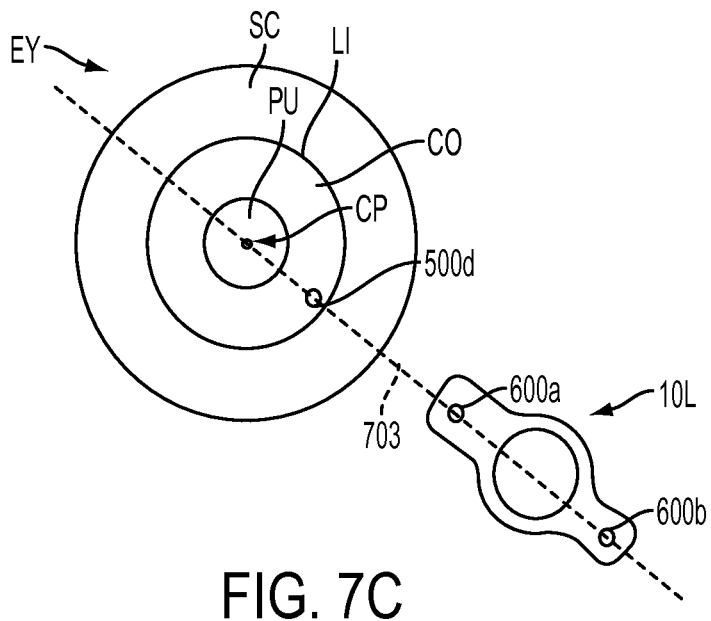

As shown in FIG. 7C, a single circular fiducials 500*d* can be generated on the periphery of the cornea CO of an eye EY. The fiducials 500*d* and the center of the pupil CP can define a line 703 which may be aligned with or parallel to the astigmatic axis of the eye EY. The artificial intraocular lens IOL can be positioned so that markers 600*a*, 600*b* on the lens IOL can be aligned with the fiducial 500*d* and pupil center CP by being on the same line 703.

Figure 7D:
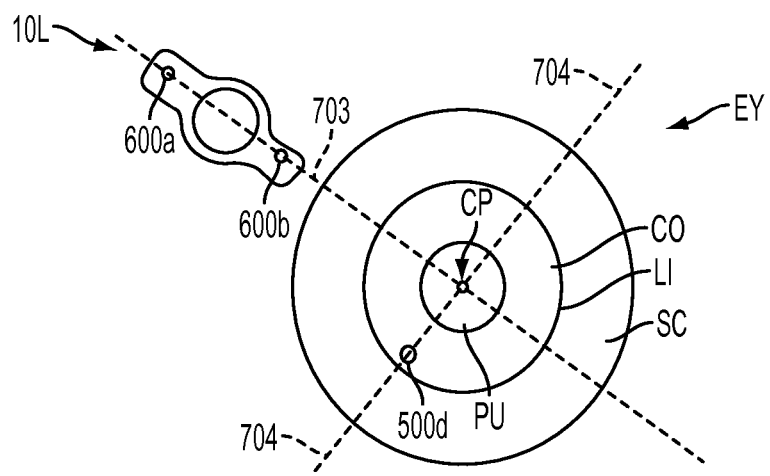

In some embodiments, the fiducial 500*d* and the pupil center CP can define a line 704 which may be perpendicular or otherwise transverse to the astigmatic axis of the eye EY. As shown in FIG. 7D, the artificial intraocular lens IOL can be positioned so that the markers 600*a*, 600*b* on the lens IOL form a line 703 perpendicular to the line 704 formed by the fiducials 500*d*1, 500*d*2. Thus, the lens IOL can be properly positioned in alignment with the astigmatic axis of the eye EY. In other embodiments, the artificial intraocular lens IOL can be positioned so that the markers 600*a*, 600*b* on the lens IOL form a line transverse to the line 703 formed by the fiducial 500*d* and the pupil center CP, for example, at predetermined angles of 30 degrees, 45 degrees, or 60 degrees.

Figure 8:
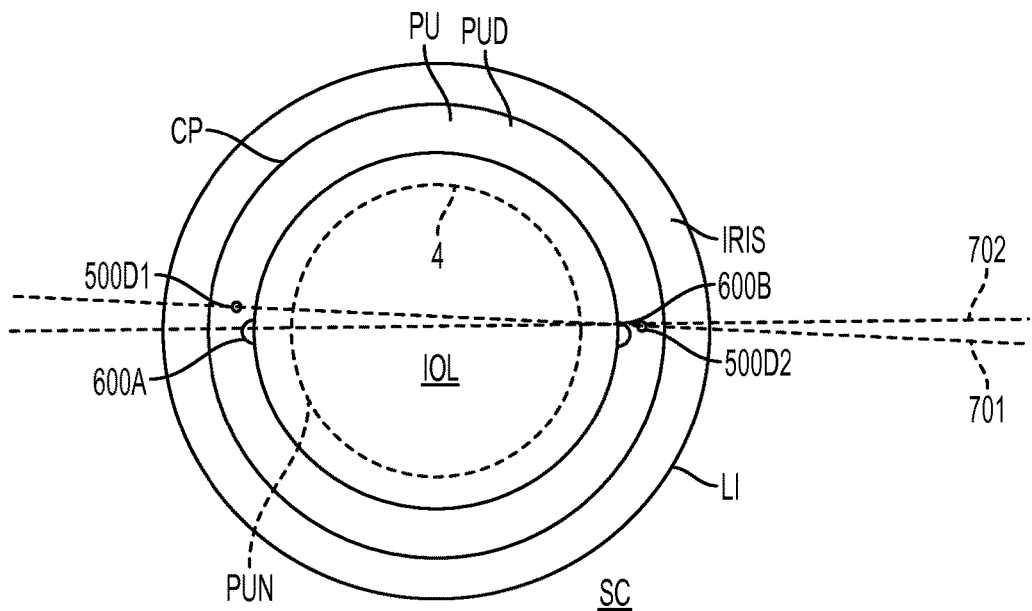
FIG. 8 shows an IOL placed in an eye, in accordance with many embodiments.

FIG. 8 shows an IOL placed in an eye, in accordance with many embodiments. The axis 701 is shown positioned relative to axis 702 to determine an alignment of the IOL. The pupil center PC is shown in relation to a center of the IOL that may or may not be marked. The two fiducials 500*d*1, 500*d*2 define a line 701 which may be aligned with or parallel to the astigmatic axis of the eye EY or other axis as described herein. The artificial intraocular lens IOL can be positioned so that markers 600*a*, 600*b* on the lens IOL can be aligned with the fiducials 500*d*1, 500*d*2 and can be on substantially the same line 701. The shape of the markers 600*a*, 600*b* can correspond to the shape of the fiducials 500*d*1, 500*d*2 as described herein.

In many embodiments, the Fiducials are located on the eye for benefit of the patient. After surgery, the lens markers 500D1 and 500D1 may not be visible under normal viewing conditions and the Fiducials 600A, 600B are placed away from the pupil of the eye to inhibit visual artifacts seen by the patient. The Fiducials 500*d*1, 500*d*2, can be placed on the cornea outside of a large natural pupil PUN of the eye that corresponds to a maximum natural pupil size such as a pupil of a dark adapted eye. Alternatively or in combination, the Fiducials may be placed on the lens capsule outside the large natural pupil PUN and within the surgically dilated pupil PUD. The large natural pupil can be, for example about 8 or 9 mm for younger patients receiving accommodating IOLs, and about 4-5 mm for older patients having cataract surgery for example. The pupil PU may be dilated during with a cycloplegic so as to comprise a dilated pupil PUD having a diameter larger than the naturally dilated pupil PUD, for example so as to allow visualization of the markers and Fiducials when the IOL is placed. The markers 600A, 600B of the IOL can be separated by a distance larger than the optical zone of the IOL, or may comprise small marks within the optical zone of the IOL.

Figure 9:
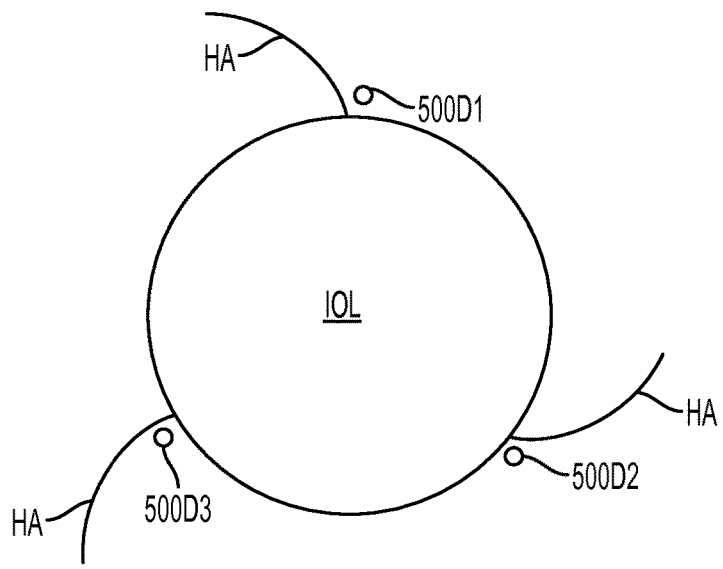
FIG. 9 shows haptics of an IOL positioned with corresponding Fiducials, in accordance with many embodiments.

FIG. 9 shows haptics of an IOL positioned with corresponding Fiducials, in accordance with many embodiments. The marks placed on the IOL can be located on one or more of an optic of the IOL or a haptic of an IOL, for example. In some embodiments, the Fiducials 500D1, 500D2, 500D3 can be placed on the eye as described herein at locations corresponding to target locations of haptics HA, for example, such that the Fiducials can be used to align the haptics for placement in the eye.

In many embodiments, an operating microscope as described herein has a magnification providing a depth of field capable of simultaneously imaging the Fiducials 500D1, 500D2 and markers 600A, 600B, and the fidicials that mark the cornea are sized and shaped to as to be visible with the markers. In many embodiments, the marks on the cornea comprise marks near the limbus, and may comprise marks formed in the limbus, conjunctiva or sclera. Alternatively or in combination, a dye can be applied to the exterior of the eye that is absorbed by the marks to improve visibility of the laser placed marks.

The methods and apparatus as described herein are suitable for combination with one or more components of laser eye surgery systems that are under development or commercially available such as:

an adaptive patient interface is described in Patent Cooperation Treaty Patent Application (hereinafter "PCT") PCT/US2011/041676, published as WO 2011/163507, entitled "ADAPTIVE PATIENT INTERFACE";

a device and method for aligning an eye with a surgical laser are described in PCT/IB2006/000002, published as WO 2006/09021, entitled "DEVICE AND METHOD FOR ALIGNING AN EYE WITH A SURGICAL LASER";

a device and method for aligning an eye with a surgical laser are described in PCT/IB2006/000002, published as WO 2006/09021, entitled "DEVICE AND METHOD FOR ALIGNING AN EYE WITH A SURGICAL LASER";

an apparatus for coupling an element to the eye is described in U.S. application Ser. No. 12/531,217, published as U.S. Pub. No. 2010/0274228, entitled "APPARATUS FOR COUPLING AN ELEMENT TO THE EYE"; and a servo controlled docking force device for use in ophthalmic applications is described in U.S. application Ser. No. 13/016,593, published as U.S. Pub. No. US 2011/0190739, entitled "SERVO CONTROLLED DOCKING FORCE DEVICE FOR USE IN OPHTHALMIC APPLICATIONS".

With the teachings described herein, a person of ordinary skill in the art can modify the above referenced devices to practice many of the embodiments described herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A method of implanting an implantable device in an eye of a patient, the method comprising:
   generating a fiducial on an anatomical structure of the eye, the anatomical structure being a portion of a cornea located outside of an area corresponding to a maximum natural size of a pupil of the eye and inside of an area having a predetermined size which is larger than the maximum natural size;
   placing the implantable device inside the eye, the implantable device having a marker located outside of the area corresponding to the maximum natural size of the pupil and inside of the area having the predetermined size;
   dilating the pupil to the predetermined size which is larger than the maximum natural size;
   visualizing the marker and the fiducial while the pupil is dilated; and
   positioning the implantable device so that the marker of the implantable device is in a positional relationship relative to the fiducial,
   wherein one of the fiducial and the marker has an empty outline shape, and the other one of the fiducial and the marker has a filled shape that corresponds to and fits within the empty outline shape.

2. The method of claim 1, wherein the eye is retained with a patient interface coupled to the eye with suction and wherein the fiducial is generated when the eye is retained with the patient interface.

3. The method of claim 1, wherein the implantable device comprises an intraocular lens and wherein the marker and the fiducial are visible to a user with a camera image or an operating microscope image provided to the user when the intraocular lens has been placed.

4. The method of claim 1, further comprising:
   receiving a user input of a treatment axis of an astigmatism of the eye;
   generating another fiducial on the anatomical structure of the eye, wherein the fiducial and the other fiducial collectively define the treatment axis and wherein the implantable device has another marker placed on opposite sides of the implantable device with respect to the marker, wherein the marker and the other marker define a lens axis of an intraocular lens and wherein the marker, the other marker, the fiducial and the other fiducial are visible to a user to determine an alignment of the treatment axis with the lens axis.

5. The method of claim 4, wherein the marker, the other marker, the fiducial and the other fiducial are displayed in an image visible to a user.

6. The method of claim 1, wherein a measurement structure of the eye is measured with a laser system when the patient has been placed on a patient support of the laser system and wherein the fiducial is generated on the anatomical structure of the eye in response to the orientation of the measurement structure.

7. The method of claim 6, wherein the measurement structure of the eye comprises one or more of a cornea of the eye, an iris of the eye or a crystalline lens of the eye and wherein the orientation comprises one or more of an angle of an astigmatic axis of the cornea, a rotational angle of the iris about a pupil of the eye or an astigmatic axis of the lens of the eye.

8. The method of claim 1, wherein the implantable device comprises an artificial intraocular lens and the positional relationship comprises a pre-determined positional relationship.

9. The method of claim 8, wherein the artificial intraocular lens comprises a toric intraocular lens.

10. The method of claim 1, wherein the implantable device is positioned so that the marker in the positional relationship relative to the fiducial is configured to align a vision correcting axis of the implantable device with an aberration axis of the eye.

11. The method of claim 10, wherein the aberration axis of the eye comprises an astigmatic axis.

12. The method of claim 10, wherein the aberration axis of the eye comprises an axis of a higher order aberration and the implantable device corrects a higher order aberration of the eye comprising one or more of coma, trefoil or spherical aberration.

13. The method of claim 1, wherein the fiducial placed on the anatomical structure of the eye has a shape comprising one of a dot, a rectangle, an arrow, a cross, a trapezoid, a square, a chevron, a pentagon, a hexagon, a circle, an ellipse, or an arc.

14. The method of claim 1, wherein the market of the implantable device has a shape comprising one of a dot, a rectangle, an arrow, a cross, a trapezoid, a square, a chevron, a pentagon, a hexagon, a circle, an ellipse, or an arc.

15. The method of claim 1, wherein the fiducial is generated on the anatomical structure of the eye by marking the anatomical structure with a laser.

16. The method of claim 1 wherein placing a fiducial on an anatomical structure of the eye comprises generating at least two fiducials on the anatomical structure of the eye.

17. The method of claim 16, wherein the at least two fiducials generated on the anatomical structure of the eye comprises a first fiducial and a second fiducial.

18. The method of claim 17, wherein a shape of the first fiducial is different from a shape of the second fiducial.

19. The method of claim 17, wherein a shape of the first fiducial is the same as a shape of the second fiducial.

20. The method of claim 16, wherein the at least two fiducials form a line corresponding to an axis of the eye and wherein the implantable device comprises at least two marks to determine a centration of the lens with respect to a pupil of the eye when the at least two marks, are positioned near the at least two fiducials.

21. The method of claim 20, wherein the axis comprises an astigmatic axis of the eye.

22. The method of claim 20, wherein the line formed from the at least two fiducials is aligned with, parallel to, transverse to, or perpendicular to the axis of the eye.

23. The method of claim 1, wherein the fiducial is created on the anatomical structure prior to coupling the eye to a patient interface.

* * * * *